United States Patent [19]

Rossetti et al.

[11] 4,217,278

[45] Aug. 12, 1980

[54] 3-NITRO-RIFAMYCINS S AND SV

[75] Inventors: Vittorio Rossetti; Leonardo Marsili; Carmine Pasqualucci, all of Milan, Italy

[73] Assignee: Archifar Laboratori Chimico Farmacologici S.p.A., Milan, Italy

[21] Appl. No.: 16,080

[22] Filed: Feb. 28, 1979

Related U.S. Application Data

[63] Continuation-in-part of Ser. No. 16,006, Feb. 28, 1979.

[30] Foreign Application Priority Data

Mar. 9, 1978 [GB] United Kingdom ............... 9294/78

[51] Int. Cl.$^2$ ............................................. C07D 413/04
[52] U.S. Cl. ............................................... 260/239.3 P
[58] Field of Search ................................... 260/239.3 P

[56] References Cited

FOREIGN PATENT DOCUMENTS

2548128  5/1976  Fed. Rep. of Germany .... 260/239.3 P

OTHER PUBLICATIONS

Dampier et al. "J. Am. Chem. Soc." vol. 98, No. 22 pp. 7064–7069 (1976).
March "Advanced Organic Chemistry" pp. 341, 488–494 (McGraw-Hill)(1968).
Morrison and Boyd "Organic Chemistry" (3rd ed) pp. 826–832 (Allyn and Bacon)(1973).

*Primary Examiner*—John M. Ford
*Assistant Examiner*—Robert T. Bond
*Attorney, Agent, or Firm*—Oblon, Fisher, Spivak, McClelland & Maier

[57] ABSTRACT

3-nitro-rifamycins S and SV useful as starting compounds for the production of antibiotic substances. Such compounds are obtained by reaction of a 3-bromo-rifamycin S with sodium nitrite in a dipolar aprotic solvent at a temperature from room temperature to +40° C.

4 Claims, No Drawings

3-NITRO-RIFAMYCINS S AND SV

This application is a Continuation-In-Part of application Ser. No. 16,006, filed Feb. 28, 1979.

The present invention relates to new 3-nitro-rifamycins S and SV useful as starting compounds for the production of useful antibiotic substances.

More particularly the present invention concerns 3-nitro-rifamycins S of formula:

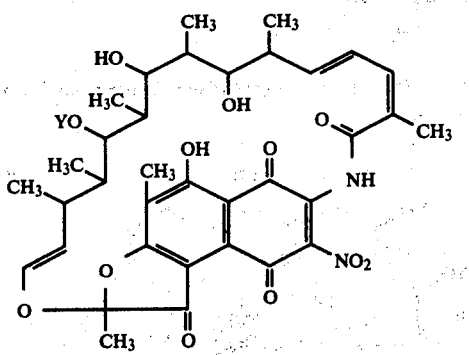

and their hidroquinonic derivatives 3-nitro-rifamycins SV of formula

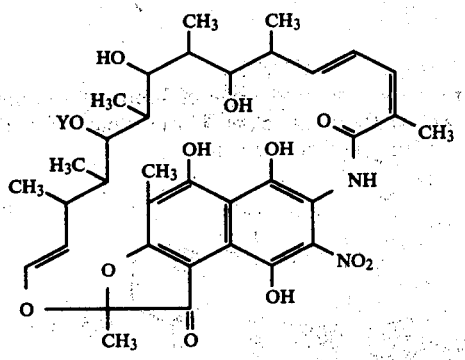

wherein Y is —H or —COCH$_3$

The 3-nitro-rifamycins S of formula (I) are obtained by reacting a 3-bromo-rifamycin S of formula:

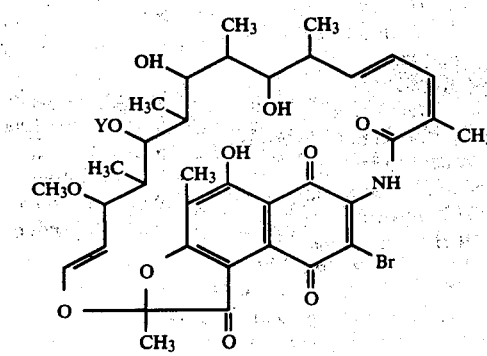

wherein Y is —H or —COCH$_3$
with sodium nitrite in dipolar aprotic solvent according to the scheme

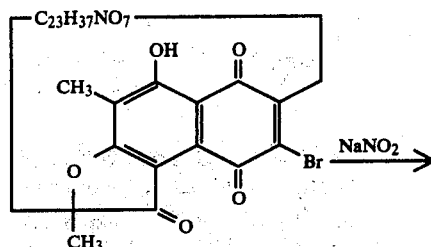

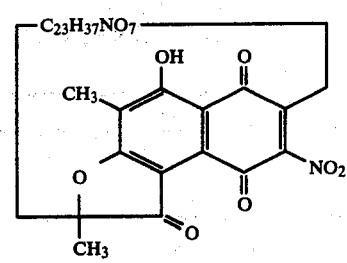

at a temperature ranging from room temperature to 40° C. and isolating the so formed compound by usual techniques.

The compounds of formula (II) are obtained by mild reduction by means of ascorbic acid of the compounds of formula (I).

The 3-bromo-rifamycins S of formula (III) are per se well known and are described in the German Patent application DOS 2548128. The compounds of formula (I) and (II) per se have not a practical interest as antibiotic substances, but they have shown to be suitable as intermediates or starting material for the production of valuable antibiotic compounds obtained by taking advantages of the reactivity of their nitro-group.

In order to be more clearly understood, the characteristic features of the present invention, the process for obtaining such compounds will now be described by mere way of unrestrictive examples.

The thin layer chromatographies referred to in the Examples as Rf are carried out on silica gel plates by using benzene:ethyl acetate:methanol (20:8:7 v/v) as eluent.

Infrared spectra are performed in vaseline oil (nujol) mull.

EXAMPLE 1

7.8 g of 3-bromo-rifamycin S are dissolved in 50 ml of N,N-dimethyl-formamide and are reacted with 0.82 g of sodium nitrite while stirring: the temperature rises spontaneously to 30° C. and stirring is continued at this temperature for 45 minutes.

The reaction mixture is diluted with 500 ml of dichloromethane and washed several times with water: the dichloromethane solution is dried over sodium sulfate and evaporated to dryness at reduced pressure.

The residue is crystallized from ethanol to give 4.8 g of pure 3-nitro-rifamycin S in orange crystals. Rf. 0.63

I.R. 3350, 1740, 1705, 1630, 1605, 1550, 1485, 1415, 1320, 1270, 1205, 1185, 1170, 1130, 1090, 1060, 970, 915 e 825 cm$^{-1}$.

U.V. (CHCl$_3$): 402 nm (E$_{1\ cm}$1% 68); 272 nm (E$_{1\ cm}$1% 336); 224 nm (E$_{1\ cm}$1% 434).

P.M.R. (CDCl$_3$), δ (using TMS as internal standard): 0.24, 0.68, 0.87 and 0.99 (4 d, CH$_3$

1.73 (s, CH$_3$-13), 2.03 (s, CH$_3$-30 and CH$_3$-COO), 2.35 (s, CH$_3$-14), 3.13 (s, CH$_3$O), 4.73 (broad d, H-25), 5.03 (dd, H-28), 6.05 - 6.60 (m, H-17, H-18, H-19 and H-29), 8.38 (s, NH) and 12.44 (S, OH-8);

Elemental analysis: for C$_{37}$H$_{44}$N$_2$O$_{14}$

|   | Calc. % | found % |
|---|---------|---------|
| C | 59.99   | 59.79   |
| H | 5.99    | 6.12    |
| N | 3.78    | 3.77    |

The same product is obtained using dimethylsulfoxide as solvent.

EXAMPLE 2

8 g of 3-nitro-rifamycin S are dissolved in 320 ml of chloroform and, while stirring at room temperature, a solution of 8 g of ascorbic acid in 20 ml of water is added; stirring is continued until the thin layer chromatography shows a complete reduction. The reaction mixture is decanted and chloroform layer is separated and washed several times with water, then dried over magnesium sulfate and evaporated to dryness at reduced pressure, the residue is then crystallized from methanol to give 6.9 g of 3-nitro-rifamycin SV in orange crystals.

Rf. 0.31

I.R. 3350 (b), 1740 (sh), 1720, 1710 (sh), 1665 (sh), 1655 (sh), 1605, 1575 (sh), 1550, 1340, 1320, 1290, 1250, 1220, 1170, 1125, 1100, 1060, 1050 (sh), 1015, 970, 945, 890, 840 and 805 cm$^{-1}$. U.V. (HCl N/10 in methanol): 436 nm (E$_1$ $_{cm}$$^{1\%}$ 102), 300 nm (E$_1$ $_{cm}$$^{1\%}$ 265).

EXAMPLE 3

3 g of 3-bromo-25-deacetyl-rifamycin S are dissolved in 30 ml of N,N-dimethyl-formamide and reacted with 0.6 ml of triethylamine and 0.4 g of sodium nitrite at room temperature in nitrogen atmosphere for 70 minutes; the reaction mixture is diluted with 50 ml of dichloromethane and washed with a 5% solution of citric acid several times; the dichloromethane solution is dried over sodium sulfate and evaporated to dryness and crystallized from methanol to give 1.8 g of pure 3-nitro-25-deacetyl-rifamycin S.

Rf. 0.55

I.R. 3350, 1739, 1705, 1660, 1650, 1625, 1600, 1550, 1480, 1320, 1295, 1260, 1200, 1180, 1160, 1125, 1060, 970, 915, and 820 cm$^{-1}$.

What we claim is:

1. 3-nitro-rifamycins S of formula

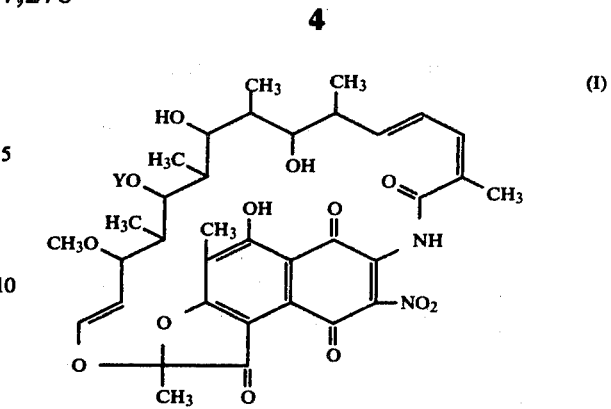

and their hydroquinonic derivatives 3-nitro-rifamycin SV of formula

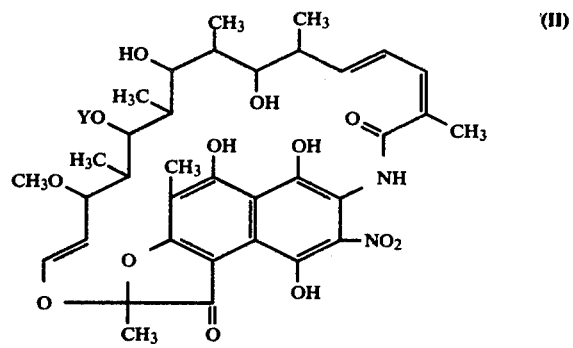

wherein Y is —H or —COCH$_3$.

2. A process for the production of 3-nitro-rifamycins of formula (I) according to claim 1, according to which a 3-bromo-rifamycin S of formula

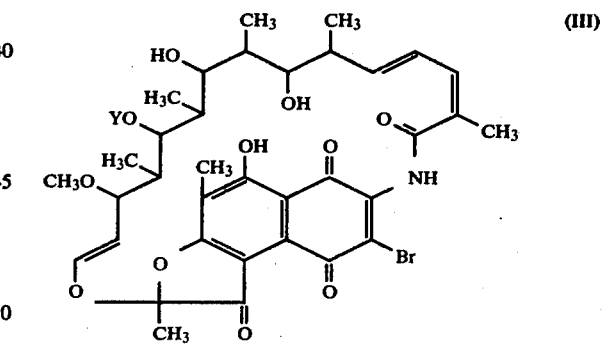

wherein Y is —H or —COCH$_3$ is reacted with sodium nitrite in a dipolar aprotic solvent at a temperature ranging from room temperature to 40° C. and isolating the so formed compound by usual techniques.

3. A process according to claim 2, wherein said dipolar aprotic solvent is selected from the group consisting of dimethyl formamide and dimethyl sulfoxide.

4. A process for the production of 3-nitro-rifamycins SV of formula II according to claim 1, wherein 3-nitro-rifamycins S of formula (I) are submitted to mild reduction by means of ascorbic acid.

* * * * *